United States Patent [19]
Fischer et al.

[11] Patent Number: 6,121,481
[45] Date of Patent: Sep. 19, 2000

[54] PROCESS FOR PREPARING 6-AMINOCAPRONITRILE

[75] Inventors: Rolf Fischer, Heidelberg; Rocco Paciello, Bad Dürkheim; Michael Röper, Wachenheim; Werner Schnurr, Herxheim, all of Germany

[73] Assignee: BASF Aktiengesellschaft, Ludwigshafen, Germany

[21] Appl. No.: 09/230,837

[22] PCT Filed: Jul. 23, 1997

[86] PCT No.: PCT/EP97/03987

§ 371 Date: Feb. 1, 1999

§ 102(e) Date: Feb. 1, 1999

[87] PCT Pub. No.: WO98/05631

PCT Pub. Date: Feb. 12, 1998

[30] Foreign Application Priority Data

Aug. 3, 1996 [DE] Germany ............... 196 31 522

[51] Int. Cl.[7] .................................. C07C 253/00
[52] U.S. Cl. ............................................. 558/452
[58] Field of Search ................................. 558/452

[56] References Cited

U.S. PATENT DOCUMENTS 2,777,873  1/1957  Hasek .
3,461,167  8/1969  Buchler et al. .
3,471,563  10/1969  Brake .
5,068,398  11/1991  Merger et al. .

FOREIGN PATENT DOCUMENTS 011 401  5/1980  European Pat. Off. .
376 121  7/1990  European Pat. Off. .

*Primary Examiner*—Deborah C. Lambkin
*Assistant Examiner*—Joseph Murray
*Attorney, Agent, or Firm*—Keil & Weinkauf

[57] ABSTRACT

The invention concerns a process for the preparation of 6-aminocapronitrile or 6-aminocapronitrile-hexamethylene diamine mixtures by: a) reacting 5-formylvaleronitrile with ammonia and hydrogen in the presence of hydrogenation catalysts selected from the group consisting of metals or metal compounds rhenium, copper and elements of group VIII of the periodic table of elements, a hydrogenation discharge product being obtained; and b) extracting from the hydrogenation discharge product 6-aminocapronitrile and optionally hexamethylene diamine, provided that the hydrogenation catalyst does not contain copper, nickel or copper and nickel as it's only components.

14 Claims, No Drawings

PROCESS FOR PREPARING 6-AMINOCAPRONITRILE

This Application is A 371 of PCT/EP97/03981 filed on Jul. 23, 1997.

DESCRIPTION

The present application relates to a process for the preparation of 6-aminocapronitrile or 6-aminocapronitrile/hexamethylene diamine mixtures starting from 5-formylvaleronitrile.

EP-A 11,401 describes the reductive amination of δ-cyanovaleraldehyde to produce hexamethylene diamine. According to Example 4 of the cited application a mixture containing 60% of δ-cyanovaleraldehyde was caused to react with ammonia and hydrogen at a temperature of 100° C. and a hydrogen pressure of 140 bar in the presence of Raney nickel over a period of two hours, the conversion (based on the δ-compound) being only 25%. The low degree of conversion demonstrates that the aminating hydrogenation of an aldehyde group and the hydrogenation of a nitrile group in the same molecule to form a diamine represent a difficult hydrogenation problem. Furthermore the formation of 6-aminocapronitrile is not described. Furthermore the on-stream time of the catalyst used is unsatisfactory for economic exploitation.

U.S. Pat. No. 2,777,873 reveals that it is possible to perform aminating hydrogenation on 5-formyl valerate using ammonia and hydrogen in the presence of nickel, cobalt, iron, platinum, or palladium catalysts at from 100° to 160° C. and under pressures ranging from 1 to 1000 atmospheres to produce 6-aminocaproates. EP-A 376,121 describes this reaction also for ruthenium catatysts, the process being carried out at temperatures ranging from 80° to 140° C. and under pressures ranging from 40 to 1000 bar.

Cobalt, copper, and rhenium catalysts are suitable for the hydrogenation of adipodinitrile to hexamethylene diamine in the presence of ammonia, as stated in U.S. Pat. No. 3,461,167, column 3, lines 66 to 74. The process is preferably operated at from 70° to 170° C. and from 300 to 7000 psi. According to U.S. Pat. No. 3,471,563 ruthenium catalysts can also be used for this reaction.

Thus Group VIIIb elements hydrogenate both nitrile and aldehyde groups to produce amino groups.

It is thus an object of the present inventionto provide a process which makes it possible to prepare, starting from 5-formylvaleraldehyde, either 6-aminocapronitrile or a mixture of 6-aminocapronitrile and hexamethylene diamine at a very high conversion rate. A particular object of the invention is to find a process which guarantees long on-stream times of the catalysts.

Accordingly, there has been found a process for the preparation of 6-aminocapronitrile or a mixture of 6-aminocapronitrile and hexamethylene diamine, in which
a) 5-formylvaleronitrile is caused to react with ammonia and hydrogen in the presence of hydrogenation catalysts selected from the group consisting of metals or metal compounds of rhenium, copper and Group VIIIb elements, giving a hydrogenation effluent, and
b) 6-aminocapronitrile and possibly hexamethylene diamine is/are isolated from the hydrogenation effluent,
provided that the hydrogenation catalyst does not contain copper, nickel, or copper and nickel as sole components.

The starting compound used in the process of the invention is 5-formylvaleraldehyde. The patent literature reveals a number of possibilities for the preparation of 5-formylvaleronitrile:

WO 94/26688 describes a process, in which
(a) internal substituted olefins are isomerized to form terminal olefins,
(b) the terminal olefins are preferably hydroformylated in the presence of the internal olefins,
(c) the products of the hydroformylation are separated and
(d) the internal olefins are recycled to the isomerization stage.

In claim 3 of the cited WO 94/26688 there are claimed nitrile-containing olefins. The hydroformylation catalysts used are rhodium/triphenylphosphine systems, in which the triphenylphosphine is rendered soluble in water by suitable functional groups.

WO 95/18783 describes the hydroformylation of internal nitrile-containing olefins using water-soluble platinum catalysts.

EP-A 11,401 also reveals that it is possible to cause 3-pentenenitrile to react with carbon monoxide and hydrogen under pressure in the presence of a cobalt catalyst. During this procedure there is formed a mixture of isomeric formylvaleronitriles and the alcohols corresponding to the aldehyde group.

5-Formylvaleronitrile is caused, in the process of the invention, to react at temperatures ranging from 40° to 150° C., advantageously from 50° to 140° C. and more advantageously from 60° to 130° C., and pressures ranging from 2 to 350 bar, advantageously from 20 to 300 bar and more advantageously from 40 to 250 bar, with ammonia and hydrogen in the presence of hydrogenation catalysts in a first step (stage a)) giving a hydrogenation effluent.

The reaction is carried out preferably in liquid ammonia acting as solvent, in which case the ammonia simultaneously serves as reactant. The amount of ammonia is usually from 1 to 80 mol and in particular from 10 to 50 mol of ammonia per mole of 5-formylvaleronitrile. It may also be advantageous to use, in addition to ammonia, a solvent inert under the reaction conditions, such as an alcohol, ester, ether, or hydrocarbon, in which case a ratio by weight of solvent to 5-formylvaleronitrile ranging from 0.1:1 to 5:1 and preferably from 0.5:1 to 3:1 is generally used. Alcohols such as methanol and ethanol are particularly preferred.

The amount of hydrogen employed is usually such that the molar ratio of hydrogen to 5-formylvaleronitrile ranges from 1:1 to 100:1 and preferably from 5:1 to 50:1.

The catalysts used in the process of the invention are hydrogenation catalysts, which are selected from the group consisting of metals or metal compounds of rhenium, copper, and the Group VIIb elements (referred to below as "hydrogenating metals"), preferably iron, cobalt, nickel, ruthenium, rhodium, palladium, osmium, iridium, and platinum, more preferably ruthenium, cobalt, palladium, and nickel, provided that the hydrogenation catalyst does not contain copper, nickel, or copper and nickel as sole components.

The catalysts used in the process of the invention can be solid catalysts or supported catalysts. Examples of suitable support materials are porous oxides such as aluminum oxide, silicon dioxide, aluminum silicates, lanthanum oxide, titanium dioxide, zirconium dioxide, magnesium oxide, zinc oxide and zeolites and also activated charcoals or mixtures of said compounds.

The catalysts can be used as fixed-bed catalysts for ascending or descending reactants or as suspension catalysts. The space velocity used is preferably in the range of from 0.1 to 2.0 and more preferably from 0.3 to 1 kg of 5-formylvaleronitrile per liter of catalyst per hour.

Another possibility is to use compounds of the aforementioned metals as homogeneously dissolved hydrogenation catalysts.

In a preferred embodiment, the homogeneously dissolved catalysts can furthermore contain from 0.01 to 25 wt % and preferably from 0.1 to 5 wt %, based on the total amount at hydrogenating metals (calculated as elements), of at least one promotor based on a metal selected from the group consisting of copper, silver, gold, manganese, zinc, cadmium, lead, tin, scandium, yttrium, lanthanum and the lanthanide elements, titanium, zirconium, hafnium, chromium, molybdenum, tungsten, vanadium, tantalum, antimony, bismuth, and aluminum, and also doped by from 0.01 to 5 wt % and preferably from 0.1 to 3 wt %, based on the hydrogenating metals (calculated as elements) of a compound based on an alkali metal or an alkaline earth metal, preferably alkali metal and alkaline earth metal hydroxides such as lithium hydroxide, sodium hydroxide, potassium hydroxide, rubidium hydroxide, cesium hydroxide and more preferably lithium hydroxide.

The catalysts used in the process of the invention may be, eg, so-called deposited catalysts. These catalysts can be prepared by precipitating their catalytically active components from salt solutions thereof, in particular from the solutions of their nitrates and/or acetates, for example by the addition of alkali metal and/or alkaline earth metal hydroxide and/or carbonate solutions, eg, difficultly soluble hydroxides, hydrated oxides, basic salts or carbonates, and then drying the resulting precipitates and converting them to the corresponding oxides, mixed oxides and/or mixed-valence oxides by calcination at temperatures generally ranging from 300° to 700° C. and in particular from 400° to 600° C., which oxides are usually reduced by treatment with hydrogen or hydrogen-containing gases usually at from 50° to 700° C. and in particular from 100° to 400° C. to give the respective metals and/or oxidic compounds of a lower degree of oxidation and are thus converted to the actual catalytically active form. Reduction is usually continued until no more water is formed.

In the preparation of deposited catalysts which include a support material the precipitation of the catalytically active components can take place in the presence of the desired support material. Alternatively and advantageously, however, the catalytically active components can be simultaneously precipitated with the support material from appropriate salt solutions. In the process of the invention hydrogenation catalysts are preferably used which contain the hydrogenation-catalyzing metals or metal compounds deposited on a support material. Apart from the aforementioned deposited catalysts containing the catalytically active components in addition to a support material, suitable support materials for the process of the invention are generally those onto which the hydrogenation-catalyzing components have been applied, eg, by impregnation.

The method of applying the catalytically active metals to the support is usually not crucial and can be effected in a variety of ways. The catalytically active metals can be applied to these support materials for example by impregnation with solutions or suspensions of the salts or oxides of the respective elements followed by drying and reduction of the metal compounds to the metals or compounds of a lower degree of oxidation by means of a reducing agent, preferably hydrogen or a complex hydride.

Another possibility for the application of the catalytically active metals to said supports consists in impregnating the support with solutions of thermally readily decomposable salts, eg, nitrates or thermally readily decomposable complex compounds, for example carbonyl or hydride complexes of the catalytically active metals, and heating the thus impregnated support to temperatures usually ranging from 300° to 600° C. for the purpose of thermal disintegration of the adsorbed metal compounds. This thermal disintegration is preferably carried out under a blanket of protective gas. Suitable protective gases are, for example, nitrogen, carbon dioxide, hydrogen, or a noble gas.

Furthermore the catalytically active metals can be deposited onto the catalyst support by vapor deposition or flame spraying. The weight of catalytically active metals in these supported catalysts is theoretically insignificant for the successful operation of the process of the invention. It will be obvious to the person skilled in the art that higher contents of catalytically active metals in these supported catalysts will usually provide higher space-time yields than lower contents. Supported catalysts are generally used in which the content of catalytically active metals is from 0.1 to 90 wt % and preferably from 0.5 to 40 wt %, based on the entire catalyst.

Since these contents are specified with respect to the entire catalyst including its support material, but different support materials have very different specific weights and specific surface areas, it may be possible to use lower or greater contents, however, without having any disadvantageous effect on the results achieved by the process of the invention. Of course it is possible to apply a number of catalytically active metals to the said support material. Furthermore, the catalytically active metals can be applied to the support by, for example, the processes described in DE-A 2,519,817, EP-A 1,477,219 and EP-A 285,420. In the catalysts described in said specifications the catalytically active metals are present in the form of alloys, which can be produced by thermal treatment and/or reduction of the support materials after treatment thereof with a salt or complex of said metals by, say, impregnation.

Activation of both the deposited catalysts and the supported catalysts can, if desired, take place in situ at the commencement of the reaction by means of the hydrogen present, but preferably these catalysts are activated before use.

From the hydrogenation effluent obtained in stage a) of the process of the invention there is isolated, by usual methods such as distillation, 6-aminocapronitrile, optionally together with hexamethylene diamine (stage b)).

In a preferred embodiment, the isolation of 6-aminocapronitrile and, if desired, hexamethylene diamine in stage b) is preceded by the separation of ammonia and hydrogen and, if desired, the catalyst.

In another preferred embodiment 5-formylvaleronitrile is first of all treated at temperatures ranging from 40° to 150° C. with ammonia (first stage) giving an ammoniacal effluent. This can take place for example in an upstream reactor. This reaction can take place in the absence of or, preferably, in the presence of an acidic, homogeneous or heterogeneous catalyst. In this case the space velocity (using heterogeneous catalysts) is usually from 0.1 to 2.0 kg of 5-formylvaleronitrile per liter of catalyst per hour.

The ammoniacal effluent can then, if desired, be freed from the acid catalyst (second stage).

In a third stage the ammoniacal effluent or the ammoniacal solution is caused to react with ammonia and hydrogen in the presence of hydrogenation catalysts selected from the group consisting of metals or metal compounds of the elements copper and rhenium and Group VIIIb elements, giving a hydrogenation effluent, this process usually being carried out in the same way as the process described above.

The process is followed by isolation of 6-aminocapronitrile and optionally hexamethylene diamine from the hydrogenation effluent by known methods.

The acid catalysts used can be for example zeolites in the H form, acid ion exchangers, heteropoly acids, acidic and superacidic metal oxides, which may optionally be doped with sulfate or phosphate, and inorganic or organic acids.

Examples of suitable zeolites are representatives of the mordenite group or porous erionite- or chabasite-type zeolites or faujasite-type zeolites, eg, Y-type, X-type, or L-type zeolites. This group also includes the so-called "ultra-stable" faujasite-type zeolites, ie dealuminated zeolites.

Particularly advantageous zeolites are those having a pentasil structure such as ZSM-5, ZSM-11, and ZMB-10. All of these have as basic building block a five-membered ring composed of $SiO_2$ tetrahedrons. They are characterized by a high $SiO_2/Al_2O_3$ ratio and also by pore sizes situated between those of A-type zeolites and those of X-type or Y-type zeolites.

The heteropoly acids used in the process of the invention are inorganic poly acids, which, unlike isopoly acids, possess at least two different central atoms. Examples thereof are dodecatungstophosphoric acid $H_3PW_{12}O_{40} \cdot H_2O$ and dodecamolybdophosphoric acid $H_3PMo_{12}O_{40} \cdot H_2O$. Theoretically, all of the catalysts and catalyst combinations described in EP-A 158,229 can be used.

Preferred heteropoly acids are heteropoly acids of molybdenum or tungsten with phosphoric acid, telluric acid, selenic acid, arsenic acid or silicic acid, in particular with phosphoric acid.

Some of the protons of the heteropoly acids can be replaced by metal ions, of which alkali metal and alkaline earth metal ions are preferred.

Preferred acid ion exchangers are, eg, cross-linked polystyrenes containing sulfonic acid groups.

Acid metal oxides are for example $SiO_2$, $Al_2O_3$, $ZrO_2$, $Ga_2O_3$, $PbO_2$, $Sc_2O_3$, $La_2O_3$, $TiO_2$, $SnO_3$, etc. or combinations of individual oxides. To increase their acidity, the oxides can by treated with mineral acids such as sulfuric acid, if desired.

Suitable acids are for example mineral acids such as sulfuric acid and phosphoric acid and also organic acids such as sulfonic acids.

Suitable superacidic metal oxides are, eg, sulfate-doped $ZrO_2$ or $ZrO_2$ containing molybdenum or tungsten.

In another preferred embodiment the hydrogenation is carried out over a hydrogenating metal, applied to one of said oxidic supports. Following the removal of excess hydrogen and, optionally, of the catalyst, the hydrogenation effluent is preferably worked up to 6-aminocapronitrile and possibly hexamethylene diamine by fractional distillation.

The process of the invention yields 6-aminocapronitrile at very good conversion rates and good yields and selectivities. It is also possible, by varying the temperature and space velocity, to obtain mixtures of 6-aminocapronitrile and hexamethylene diamine. Relatively high temperatures and low space velocities favor the formation of hexamethylene diamine, whilst lower temperatures and high space velocities favor the formation of capronitrile.

6-Aminocapronitrile and hexamethylene diamine are important fiber precursors. 6-Aminocapronitrile can be cyclisized to caprolactam, the intermediate for the preparation of nylon 6. Hexamethylene diamine is mostly caused to react with adipic acid to form the so-called AH salt, the intermediate for nylon 6.6.

EXAMPLES

Example 1

In an autoclave having a capacity of 300 ml and equipped with a sampling sluice (material HC 4) there were placed 11 g of 5-formylvaleronitrile and 3 g of Ru (3%) on $Al_2O_3$ (4 mm extrudates) under protective gas (argon). The autoclave was then sealed and 150 ml of $NH_3$ were forced in. Thorough mixing was effected using a magnetic stirrer. After heating to 80° C. (autogenous pressure: ca. 39 bar) the mixture was kept at 80° C. for a further 2 hours and then the overall pressure was raised, with hydrogen, to 70 bar. The pressure of 70 bar was maintained by constantly forcing in more hydrogen. After 25 hours, the autoclave was depressurized and the hydrogenation effluent analyzed by gas chromatography. The products formed comprised 73% of 6-aminocapronitrile and 12% of hexamethylene diamine. The conversion was 100%.

Example 2

In the autoclave described in Example 1 there were placed 20 g of 5-formylvaleronitrile and 3 g of Pd (2%) on $Al_2O_3$ powder and 0.41 g of lithium hydroxide under protective gas (argon). The autoclave was then sealed and 140 ml of NH3 were forced in. The mixture was stirred using a magnetic stirrer and was heated to 100° C. and the overall pressure raised to 80 bar by forcing in hydrogen and then kept at this value by continuous replenishment with hydrogen. After a period of 23 hours the autoclave was depressurized and the hydrogenation effluent analyzed by gas chromatography. The products formed comprised 59.01% of 6-aminocapronitrile and 5.1% of hexamethylene diamine (conversion 100%).

Example 3

The cobalt catalyst used in this example (23% of $Co/Al_2O_3$, 4 mm extrudates) was activated before use for the preparation of 6-aminocapronitrile by treatment under a stream of hydrogen for 2 hours at 250° C.

In the autoclave described in Example 1 there were placed 32 g of 5-formylvaleronitrile and 10 g of cobalt catalyst under argon. The autoclave was then sealed and 130 ml of ammonia were forced in. The mixture was stirred using a magnetic stirrer and was heated to 100° C. and the overall pressure raised to 100 bar by forcing in hydrogen and then kept at this value by continuous replenishment with hydrogen. After a period of 20 hours the autoclave was depressurized and the hydrogenation effluent analyzed by gas chromatography. The products formed comprised 56% of 6-aminocapronitrile and 6% of hexamethylene diamine (conversion 100%).

Preparation of 6-Aminocapronitrile

SUMMARY

The preparation of 6-aminocapronitrile or 6-aminocapronitrile/hexamethylene diamine mixtures, in which a) 5-formylvaleronitrile is caused to react with ammonia and hydrogen in the presence of hydrogenation catalysts selected from the group consisting of metals or metal compounds of rhenium, copper, and Group VIIIb elements, giving a hydrogenation effluent, and b) from the hydrogenation effluent there is isolated 6-aminocapronitrile and possibly hexamethylene diamine, provided that the hydrogenation catalyst does not contain copper, nickel, or copper and nickel as sole components.

What is claimed is:

1. A process for the preparation of 6-aminocapronitrile, wherein
   a) 5-formylvaleronitrile is reacted with ammonia and hydrogen in the presence of a hydrogenation catalyst selected from the group consisting of metals or metal compounds of iron, cobalt, nickel, ruthenium, rhodium, palladium, osmium, iridium and platinum, giving a hydrogenation effluent, and
   b) from the hydrogenation effluent there is isolated 6-aminocapronitrile,
provided that the hydrogenation catalyst does not contain nickel as sole component.

2. The process defined in claim 1, wherein the hydrogenation catalyst is selected from the group consisting of metals or metal compounds of ruthenium, cobalt, palladium and nickel.

3. The process defined in claim 1, wherein excess ammonia and hydrogen are removed in stage b) prior to the isolation of 6-aminocapronitrile.

4. The process defined in claim 3, wherein the catalyst is also removed in stage b).

5. The process defined in claim 1, further comprising
   first treating 5-formylvaleronitrile with ammonia to give an ammoniacal effluent, and
   thereafter reacting said ammoniacal effluent in stage a).

6. The process defined in claim 5, wherein said treatment of 5-formylvaleronitrile is carried out in the presence of an acid catalyst.

7. The process defined in claim 6, wherein said acid catalyst is removed from the ammoniacal effluent prior to stage a).

8. The process defined in claim 1, wherein the 6-aminocapronitrile is isolated as a mixture with hexamethylene diamine.

9. The process defined in claim 1, wherein stage a) is carried out at a temperature of from 40 to 150° C.

10. The process defined in claim 1, wherein stage a) is carried out at a pressure of from 2 to 350 bar.

11. The process defined in claim 1, wherein stage a) is carried out in liquid ammonia.

12. The process defined in claim 1, wherein stage a) is carried out in an inert solvent.

13. The process defined in claim 1, wherein the molar ratio of hydrogen to 5-formylvaleronitrile is from 1:1 to 500:1.

14. The process defined in claim 5, wherein the 5-formylvaleronitrile is treated with ammonia at a temperature of from 40 to 150° C.

* * * * *